United States Patent [19]

Murata et al.

[11] Patent Number: 4,497,701

[45] Date of Patent: Feb. 5, 1985

[54] HUMIDITY SENSITIVE DEVICE

[75] Inventors: Michihiro Murata, Kyoto; Akira Kumada, Ootsu, both of Japan

[73] Assignee: Murata Manufacturing Co., Ltd., Japan

[21] Appl. No.: 468,479

[22] Filed: Feb. 22, 1983

[51] Int. Cl.³ ............................................. G01N 27/46
[52] U.S. Cl. ...................................... 204/430; 73/335; 73/336.5; 252/194; 422/98; 204/1 T
[58] Field of Search ............... 204/1 W, 430; 252/194; 73/335, 336.5; 422/98

[56] References Cited

U.S. PATENT DOCUMENTS

| 3,545,622 | 12/1970 | Sakhnovsky et al. | 252/194 |
| 4,083,765 | 4/1978 | Lawson | 204/430 |
| 4,120,813 | 10/1978 | Hatanaka et al. | 252/194 |
| 4,295,987 | 10/1981 | Parks | 252/194 |
| 4,298,855 | 11/1981 | Mills | 422/98 |
| 4,326,414 | 4/1982 | Terada et al. | 73/336.5 |
| 4,328,478 | 5/1982 | Murata et al. | 73/335 |
| 4,373,391 | 2/1983 | Johnson | 73/336.5 |
| 4,389,328 | 6/1983 | Bellettiere et al. | 252/194 |

FOREIGN PATENT DOCUMENTS

| 2108451 | 9/1972 | Fed. Rep. of Germany | 252/194 |
| 0189487 | 11/1982 | Japan | 252/194 |
| 1174312 | 12/1969 | United Kingdom | 204/430 |

Primary Examiner—T. Tung
Attorney, Agent, or Firm—Ostrolenk, Faber, Gerb & Soffen

[57] ABSTRACT

A humidity sensitive device, including opposing electrodes formed on an insulating substrate, and a humidity sensitive film formed on the surface of the insulating substrate and at least between the opposing electrodes. The humidity sensitive film is obtained by coating on the surface of the insulating substrate a mixture including a conductive or semiconductive powder, a solid electrolyte powder and an organic polymer cross-linked by a zirconium compound and heating the same.

12 Claims, 2 Drawing Figures

HUMIDITY SENSITIVE DEVICE

BACKGROUND OF THE INVENTION

1. Field of the Invention

The present invention relates to a humidity sensitive device, and more specifically to an improvement in a material composition of a humidity sensitive film.

2. Description of the Prior Art

A humidity sensitive device is typically structured such that opposing electrodes are formed on an insulating substrate and a humidity sensitive film is formed on the surface of the insulating substrate and at least between the opposing electrodes. The humidity sensitive film comprises a material exhibiting a predetermined humidity-resistance value characteristic. Accordingly, the inherent resistance value of the humidity sensitive film is variable as a function of an ambient humidity and as a result, a humidity condition can be determined in terms of a resistance value of the humidity sensitive device.

One example of prior art humidity sensitive devices employs an organic material film such as cellulose including carbon powder. However, a disadvantage is encountered in this example that an organic material is liable to be deteriorated during the lapse of time and hence a stabilized characteristic can not be attained.

Another example of prior art humidity sensitive devices employs a metal oxide such as $Fe_2O_3$, $Fe_3O_4$, $Al_2O_3$, $Cr_2O_3$, and the like as a humidity sensitive film. A humidity sensitive film is formed by means of evaporation, sputtering and the like of such metal oxide. It has been observed that a thin film of such metal oxide is superior in absorption property. A variation of humidity is detected in terms of a change of an electrical resistance value by virtue of absorption moisture. An advantage is brought about by such a humidity sensitive film in that a response is fast. Nevertheless, a disadvantage is encountered in that a resistance value is relatively high and measurement of a low humidity is rather difficult.

A third example of prior art humidity sensitive devices utilizes a ceramic semiconductor. Although a ceramic semiconductor has a feature of excellent heat resisting property, a disadvantage is encountered in that a specific resistivity is high and the cost is expensive as compared with that in case of a humidity sensitive film using an organic resistance film of such material as enumerated in the first example.

SUMMARY OF THE INVENTION

The present invention has been made to solve the above discussed various problems encountered in the above described conventional humidity sensitive devices.

The gist of the present invention resides in a humidity sensitive device including opposing electrodes formed on an insulating substrate, and a humidity sensitive film formed on the surface of the insulating substrate and at least between the opposing electrodes, characterized in that said humidity sensitive film comprises (a) at least one of a conductive powder and a semiconductive powder, (b) a solid electrolyte powder, and (c) an organic polymer at least a part of which is cross-linked by a zirconium compound.

As the conductive powder, carbon powder and metal powder such as palladium powder and the like are utilized. As the semiconductive powder, $CrO_2$, $NiO$, $Fe_3O_4$, $ZnO$, $SnO_2$, $MnO_2$, $TiO_{2-x}$, and semiconductive titanate such as barium titanate group semiconductor, strontium titanate group semiconductor, and the like are utilized.

The solid electrolyte powder may be of the types of proton conductor and alkaline ion conductor. Of these, examples of the type of proton conductor are $H_3Mo_{12}PO_{40}.29H_2O$, $H_3W_{12}PO_{40}.29H_2O$, $H_8UO_2PO_4.4H_2O$, hydrated $H_3O^+\beta\text{-}Al_2O_3$, hydrated $H_3O^+\beta''\text{-}Al_2O_3$, $NH_4^+/H(H_2O)_x+\beta''\text{-}Al_2O_3$, $H^+$ exchange montmorillonite, $Sb_2O_5.4H_2O$, and $SnO_2.3H_2O$. Examples of the type of alkaline ion conductor are $Na^+\text{-}\beta Al_2O_3$, $Na^+\text{-}\beta''Al_2O_3$, $Na_3Zr_2PSi_2O_{12}$, $Li_{14}Zn(GeO_4)_4$, $Li_5AlO_4$, $Li_4B_7O_{12}Cl$, $LiI+40$ mol % $Al_2O_3$, $Li^+\text{-}\beta Al_2O_3$, $Li^+\text{-}\beta''Al_2O_3$, $K^+\text{-}\beta Al_2O_3$, $K^+\text{-}\beta''Al_2O_3$, $K_{1.6}Mg_{0.8}Ti_{7.2}O_6$, $K_{1.76}Al_{1.76}Ti_{7.12}O_{16}$, $Li_3VO_4$ and $Li_4GeO_4$.

As the organic polymer, at least a part of which is to be cross-linked by a zirconium compound, epoxy resin, ethyl cellulose, polyvinyl alcohol, water-soluble polymer, silicone resin, fluoric resin and the like may be utilized. The organic polymer mixed with a zirconium compound is heated, whereby a bridge is formed in at least a part of the organic polymer.

The zirconium compounds include zirconium oxychloride and zirconium acetate, and compounds denatured by hydration of these salts. The humidity sensitive film may include at least one member selected from the group of the compounds described above.

The cross-linked condition of an organic polymer by a zirconium compound can be changed depending upon a mixing ratio of both the compounds, a heating temperature or other conditions. Concerning the mixing ratio of the constituent components of the humidity sensitive film, at least one of the conductive and semiconductive powders and the solid electrolyte powder occupy the substantial parts of the constituent components, and the remaining component is the organic polymer cross-linked by a zirconium compound.

The inventive humidity sensitive device is first characterized by utilization of solid electrolyte powder.

More specifically, an advantage is brought about by the utilization of the solid electrolyte powder in that ionic conduction by adsorption of water is facilitated, and a humidity sensitive device having a large change rate of a resistance value with a humidity variation can be obtained. Furthermore, the change of a resistance value is increased in the range of a high humidity.

In humidity sensitive devices relying on ionic conduction, ions generated by absorption of moisture are liable to remain. Accordingly, if the absorption of moisture occurs again, the amount of generated ions may be increased. On the other hand, if an inactive compound is formed, the amount of generated ions may be decreased. As a result, the deterioration of the characteristic of the humidity sensitive device may be observed.

However, according to the present invention, the above described problem of the deterioration of the characteristic can be solved by the use of the solid electrolyte. The inventive humidity sensitive device has the characteristic of high reliability and less deterioration of its characteristic.

Therefore, it can be said that the inventive humidity sensitive device has less deterioration of characteristic even in a dew state and high capability of detecting as a dew sensor.

The inventive humidity sensitive device is further characterized by the utilization of a zirconium compound.

The zirconium compound is of high reactivity, and tends to result in the formation of inorganic polymer. When the zirconium compound is attached to an organic polymer having compatibility with the zirconium compound, the zirconium compound serves as a cross-linking agent to form a bridge of (—O—Zr—) to the organic polymer and makes the structure of a humidity sensitive film stable. Furthermore, it has been observed that existence of the inorganic polymer including zirconium not only strengthens the film per se in a solidified state but also largely decreases a resistance value on the occasion of a moisture being absorbed, although the resistance value of the humidity sensitive film in a dry state is very high, and thus considerably increases a variation rate of the resistance value as a function of moisture absorption. Although detailed reasoning of the above described characteristic is not clearly known, it is presumed that the enhancement of hydrophilic property of the humidity sensitive film by inclusion of a zirconium compound, as well as the ionic conductivity of the solid electrolyte, increases the variation rate of the resistance value as a function of moisture absorption.

Although a variation of an electrical resistance is observed as a function of moisture absorption even in case of only organic polymer, the resistance value is extremely high even in a moisture absorbed state and no large change of the resistance value is observed, which is a hindrance to practical use of the same. Furthermore, it is extremely difficult to obtain a variety of humidity-resistance characteristics. However, according to the present invention, a relatively large variation of a resistance value can be observed even in a low humidity state. In addition, by changing a mixing ratio of a conductive powder and/or a semiconductive powder, a solid electrolyte powder, a zirconium compound, and an organic polymer, the range of variation of the resistance value can be made large and as a result humidity sensitive devices having any desired humidity-resistance characteristics can be provided. Furthermore, the present invention can be applied to a dew sensor as well as a humidity sensor.

DESCRIPTION OF THE PREFERRED EMBODIMENTS

The inventive humidity sensitive device is usually constructed so that a humidity sensitive film is formed on an insulating substrate of such as glass, ceramic or the like so as to cover opposing electrodes formed on the insulating substrate.

Figure 1:
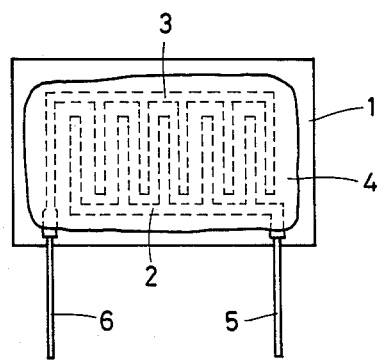
FIG. 1 is a plan view of one example of a typical humidity sensitive device.

FIG. 1 shows one example of the inventive humidity sensitive device.

The humidity sensitive device shown comprises an insulating substrate 1 and opposing electrodes 2 and 3 formed on the insulating substrate 1. The opposing electrodes 2 and 3 are configured in a comb-shape, such that tooth portions thereof are mutually interdigitated or interleaved. A humidity sensitive film 4 is formed on the insulating substrate 1 so as to cover the surface of the insulating substrate 1 where the opposing electrodes 2 and 3 are formed. As a result, the humidity sensitive film 4 is formed on the surface of the insulating substare 1 and at least between the electrodes 2 and 3. Lead terminals 5 and 6 are electrically connected to the end portions of the respective opposing electrodes 2 and 3 for the purpose of external connection.

An example of a method for forming the above described humidity sensitive film 4 on the insulating substrate 1 will be described. Starting materials are prepared at a predetermined mixing ratio and well mixed and further are mixed with solvent such as ethyl alcohol, thereby to obtain a paste like uniformly dispersed mixture. The above described paste like mixture is coated on the surface of the insulating substrate 1 where the opposing electrodes 2 and 3 are formed. Then the composite thus obtained is heated at temperatures of 100° C. to a temperature to which a zirconium compound do not decompose, and as a result a desired humidity sensitive film 4 is formed on the insulating substrate 1.

In the above described example, once the starting materials are mixed, solvent was added to provide a paste like mixture; however, alternatively solvent may be added to a zirconium compound and then other materials may be added thereto, thereby to obtain a paste like mixture.

In the following, the present invention will be further described in accordance with specific examples. It is believed that the present invention is better understood with reference to the following specific examples. However, it should be understood that the following examples are disclosed only for describing the present invention and are not by way of limitation of the present invention.

EXAMPLE 1

4.7 g of $MnO_2$ as a semiconductive powder and 3.8 g of $H_3O^+$-$\beta Al_2O_3$ as a solid electrolyte powder were added to 0.7 g of epoxy resin of acid anhydride type. Then an alcohol solution of zirconium oxychloride (0.2 g of $ZrO_2$ in terms of $ZrO_2$) was added thereto and the mixture thus obtained was well mixed and further was mixed with ethyl alcohol, thereby to obtain a paste like mixture having suitable viscosity.

The paste like mixture was coated on the surface of an insulating substrate of alumina where gold and opposing electrodes were formed. The opposing electrodes were formed with spacing of 0.5 mm.

Figure 2:
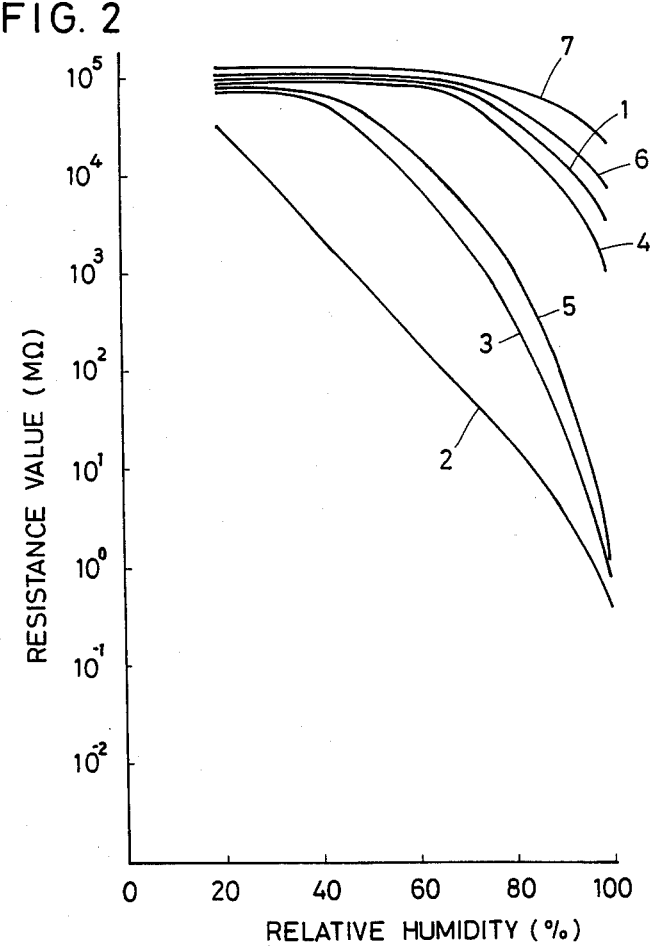
FIG. 2 is a graph showing relative humidity-resistance characteristics of humidity sensitive devices obtained by Examples 1 to 7.

The change of the resistance value of the humidity sensitive device thus obtained were measured at several relative humidities. FIG. 2 shows relative humidity-resistance characteristics of the device thus obtained. In FIG. 2, the curve denoted by the numeral 1 shows the characteristic of this example.

Furthermore, the humidity sensitive device of this example were subjected to alternating drying and dew conditions for 1500 times as applying a voltage. The following table shows initial resistance values of this example and resistance values after such tests.

|  | Resistance Value at Humidity of 70% | Resistance Value at Dew State |
|---|---|---|
| Initial Value | $1 \times 10^5$ MΩ | 460kΩ |
| Value after Test | $1 \times 10^4$ MΩ | 360kΩ |

As seen from the above table, it can be observed that the inventive humidity sensitive device has less deterioration of characteristics against the on-load life test described above.

Furthermore, the inventive humidity sensitive device has good sensitivity of detecting a dew state as compared with conventional humidity sensitive devices and can detect a low humidity state such as 20-30% of relative humidity.

EXAMPLE 2

5.2 g of $MnO_2$ as a semiconductive powder and 3.3 g of $H_3O^+$-$\beta Al_2O_3$ as a solid electrolyte powder were added to 0.7 g of epoxy resin of acid anhydride type. Then an alcohol solution of zirconium oxychloride (if in terms of $ZrO_2$, 0.6 g of $ZrO_2$) was added thereto and well mixed and further was mixed with ethyl alcohol, thereby to provide a paste like mixture of proper viscosity.

Then, as in case of Example 1, a humidity sensitive device was fabricated. The solid line 2 in FIG. 2 shows a relative humidity-resistance characteristic of Example 2 thus obtained. As seen from FIG. 2, according to Example 2, the characteristic exhibits a well proportional or linear resistance variation with respect to the relative humidity.

EXAMPLE 3

2 g of 16% solution is prepared by solving ethyl cellulose in ethylene glycol monobutyl ether. Then, 1.7 g of $MnO_2$ powder serving as a semiconductive powder and 1.4 g of $Li^+$-$\beta Al_2O_3$ powder serving as a solid electrolyte powder were added thereto and were well mixed and further an alcoholic solution of zirconium oxychloride (0.16 g of $ZrO_2$, if in terms of $ZrO_2$) was added thereto, thereby to provide a paste like mixture.

The paste like mixture is processed in the same manner as in case of Example 1, thereby to provide a humidity sensitive device. The resistance values of the humidity sensitive device thus obtained were measured at several relative humidities. The solid line 3 in FIG. 2 shows the result of the measurement.

EXAMPLE 4

In the same condition as in case of Example 3, a humidity sensitive device was fabricated, using zirconium acetate (40 mg of $ZrO_2$, if in terms of $ZrO_2$) in place of zirconium oxychloride.

The solid line 4 in FIG. 2 shows the change of the resistance value at various relative humidities.

EXAMPLE 5

1 g of 10% polyvinyl alcohol aqueous solution was prepared and 0.31 g of $MnO_2$ and 0.14 g of $H_3O^+$-$\beta Al_2O_3$ were added thereto. Then zirconium oxychloride (0.018 g of $ZrO_2$, if in terms of $ZrO_2$) was added thereto and was well mixed. The paste like mixture thus obtained was processed in the same manner as in case of Example 1, thereby to provide a humidity sensitive device. The heating condition was 20 minutes at 120° C.

The solid line 5 in FIG. 2 shows the change of the resistance value of the humidity sensitive device thus obtained at several relative humidities.

EXAMPLE 6

4.7 g of $MnO_2$ and 3.8 g of $Na^+$-$\beta Al_2O_3$ were added to 0.7 g of epoxy resin of acid anhydride type. Then an alcoholic solution of zirconium oxychloride (0.2 g of $ZrO_2$, in terms of $ZrO_2$) was added thereto and the mixture was well mixed, thereby to provide a paste like mixture. The paste thus obtained was processed in the same manner as in case of Example 1, thereby to fabricate a humidity sensitive device.

The resistance values of the humidity sensitive device thus obtained were measured at various relative humidities. The solid line 6 in FIG. 2 shows the characteristics of this humidity sensitive device. The resistance value at a dew state was 500 kΩ.

EXAMPLE 7

8.5 g of $H_3O^+$-$\beta Al_2O_3$ was added to 0.7 g of expoxy resin of acid anhydride type and an alcohol solution of zirconium oxychloride (0.2 g of $ZrO_2$, if in terms of $ZrO_2$) was added thereto. The mixture was well mixed. The paste thus obtained was processed in the same manner as in case of Example 1, thereby to fabricate a humidity sensitive device.

The resistance values of the humidity sensitive device thus obtained were measured at several relative humidities. FIG. 2 shows the result of the measurement. In FIG. 2, the line denoted by the numeral 7 corresponds to this example. This humidity sensitive device exhibits 400 kΩ of a resistance value in a dew state, which is higher than the other humidity sensitive devices.

As seen from the above described examples, according to the inventive humidity sensitive devices, it is possible to control humidity-resistance characteristics by adjusting a mixing ratio of respective materials for forming a humidity sensitive film and, therefore, the range of variation of the resistance value can be made either large or small as desired and both a humidity sensor and a dew sensor can be arbitrarily obtained. Furthermore, since a solid electrolyte is included in the humidity sensitive film, the deterioration of characteristics depending on ionic conduction can be avoided, thereby to provide a humidity sensitive device of high reliability. In addition, since the humidity sensitive film includes an organic polymer cross-linked by a zirconium compound, the humidity sensitive film per se is strengthened and, therefore, has advantage of less time dependent deterioration of characteristics. Furthermore, the enhancement of hydrophilic property of the humidity sensitive film due to the zirconium compound together with the ionic conductivity due to the solid electrolyte can provide a humidity sensitive device having excellent humidity sensitive characteristics.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A humidity sensitive device comprising an insulating substrate, first and second electrodes formed on the surface of said insulating substrate and spaced from each other, and a humidity sensitive film formed on the surface of said insulating substrate and covering at least the position of said surface located between said electrodes, characterized in that said humidity sensitive film comprises: (a) at least one of a conductive powder and a semiconductive powder; (b) a solid electrolyte powder; and (c) an organic polymer at least a part of which is cross-linked by a zirconium compound.

2. A humidity sensitive device in accordance with claim 1, wherein said solid electrolyte powder is powder of at least one of a proton conductor and an alkaline ion conductor.

3. A humidity sensitive device in accordance with claim 2 wherein said proton conductor is selected from the group consisting of: $H_3Mo_{12}PO_{40}\cdot 29H_2O$, $H_3W_{12}PO_{40}\cdot 29H_2O$, $H_8UO_2PO_4\cdot 4H_2O$, hydrated $H_3O^+\beta\text{-}Al_2O_3$, hydrated $H_3O^+\beta''\text{-}Al_2O_3$, $NH_4^+/H(H_2O)_x{}^+\beta''\text{-}Al_2O_3$, $H^+$ exchange montmorillonite, $Sb_2O_5\cdot 4H_2O$, and $SnO_2\cdot 3H_2O$, and wherein said alkaline conductor is selected from the group consisting of: $Na^+\text{-}\beta Al_2O_3$, $Na^+\text{-}\beta''Al_2O_3$, $Na_3Zr_2PSi_2O_{12}$, $Li_{14}Zn(GeO_4)_4$, $Li_5AlO_4$, $Li_4B_7O_{12}Cl$, $LiI+40$ mol % $Al_2O_3$, $Li^+\text{-}\beta Al_2O_3$, $Li^+\text{-}\beta''Al_2O_3$, $K^+\text{-}\beta Al_2O_3$, $K^+\text{-}\beta''Al_2O_3$, $K_{1.6}Mg_{0.8}Ti_{7.2}O_6$, $K_{1.76}Al_{1.76}Ti_{7.12}O_{16}$, $Li_3VO_4$ and $Li_4GeO_4$.

4. A humidity sensitive device in accordance with claim 4, wherein said zirconium compound is at least one member selected from the group consisting of zirconium oxychloride and zirconium acetate.

5. A humidity sensitive device in accordance with claim 5 wherein said conductive powder is selected from the group consisting of carbon and palladium powders and wherein said semi-conductive powder is selected from the group consisting of $CrO_2$, $NiO_2$, $Fe_3O_4$, $ZnO$, $SnO_2$, $MnO_2$ and titanate powder.

6. A humidity sensitive device in accordance with claim 6 in which said organic polymer is selected from the group consisting of epoxy resin, ethyl cellulose, polyvinyl alcohol, silicone resin and fluoric resin.

7. A humidity sensitive device in accordance with claim 2, wherein said zirconium compound is at least one member selected from the group consisting of zirconium oxychloride and zirconium acetate.

8. A humidity sensitive device in accordance with claim 1, wherein said zirconium compound is at least one member selected from the group consisting of zirconium oxychloride, zirconium acetate, and those zirconium compounds denatured by hydration.

9. A humidity sensitive device in accordance with claim 1, containing $MnO_2$ semi-conductive powder.

10. A humidity sensitive device in accordance with claim 9 containing $H_3O^+\text{-}\beta Al_2O_3$ as said solid electrolyte powder and an epoxy resin or polyvinyl alcohol crosslinked by zirconium oxychloride.

11. A humidity sensitive device in accordance with claim 9 containing $Li^+\text{-}\beta Al_2O_3$ as said solid electrolyte powder and ethyl cellulose crosslinked by zirconium oxychloride or zirconium acetate.

12. A humidity sensitive device in accordance with claim 9 containing $Na^+\text{-}\beta Al_2O_3$ as said solid electrolyte powder and an epoxy resin crosslinked by zirconium oxychloride.

* * * * *